United States Patent [19]
Royse

[11] Patent Number: 4,572,182
[45] Date of Patent: Feb. 25, 1986

[54] NOTCHED PRESSURE PAD FOR AN ARTERY CLAMP

[75] Inventor: Suzanne M. Royse, Beaverton, Oreg.

[73] Assignee: Instromedix, Inc., Beaverton, Oreg.

[21] Appl. No.: 566,169

[22] Filed: Dec. 27, 1983

[51] Int. Cl.$^4$ .............................................. A61B 17/12
[52] U.S. Cl. .................................... 128/325; 128/346; 604/116
[58] Field of Search ............... 128/325, 346; 604/115, 604/116

[56] References Cited

U.S. PATENT DOCUMENTS

| 1,561,116 | 11/1925 | Silliman | 128/325 |
| 2,712,314 | 7/1955 | Kohl | 604/116 |
| 3,779,249 | 12/1973 | Semler | 128/346 |
| 4,314,568 | 2/1982 | Loving | 604/116 |

FOREIGN PATENT DOCUMENTS 2447713 10/1980 France ................. 128/325

Primary Examiner—Gene Mancene
Assistant Examiner—John G. Weiss
Attorney, Agent, or Firm—Kolisch, Hartwell & Dickinson

[57] ABSTRACT

A notched pressure pad for use on an artery clamp of the type used to apply pressure following catheterization of a major artery. The pad includes a notched portion to facilitate placement of the pad over a catheter prior to removal of a catheter from a patient's artery. The pad is removably attached to an artery clamp.

4 Claims, 3 Drawing Figures

NOTCHED PRESSURE PAD FOR AN ARTERY CLAMP

BACKGROUND AND SUMMARY OF THE INVENTION

This invention relates generally to a pressure pad which is used with an artery clamp in a surgical procedure. In particular, the invention relates to a pressure pad with a notched portion extending inwards from its periphery which facilitates the withdrawal of a catheter from an artery following a surgical procedure.

The pressure pad of the instant invention may be used with an artery clamp such as that described in U.S. Pat. No. 3,779,249 issued to Semler. The artery clamp and pad are used to apply pressure to a puncture point on a major artery following any surgical procedure where it has been necessary to catheterize the artery. Following withdrawal of an arterial catheter, or needle, pressure should be applied to the puncture site for approximately 6-12 minutes. While the pad described by Semler in the cited patent provides pressure at the desired point once the catheter has been withdrawn, it has been found that the catheter must be completely withdrawn prior to the application of pressure to the point of catheter entry. This results in a brief, but vigorous, free flow of blood through the puncture site, which may obscure the exact location of the puncture, and make placement of the clamp and its associated pressure pad difficult.

Accordingly, an object of the invention is to provide a pressure pad which may be accurately positioned adjacent a puncture site prior to removal of a catheter.

Another object of the invention is to provide a pressure pad which is usable with existing artery clamps.

The pad of the instant invention includes a notched portion which facilitates placement of the pad over a puncture site prior to removal of a catheter. The pad may be used with existing artery clamps.

These and other objects and advantages of the pressure pad of the invention will become more apparent as the description which follows is read in conjunction with the accompanying drawings.

DETAILED DESCRIPTION OF THE INVENTION

Figure 1:
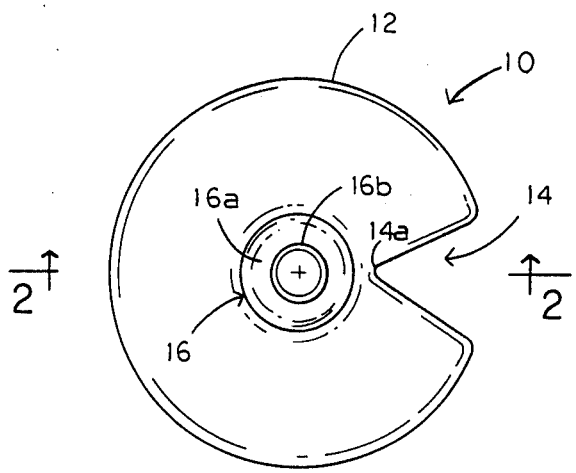
FIG. 1 is a top plan view of a pressure pad.
Figure 2:
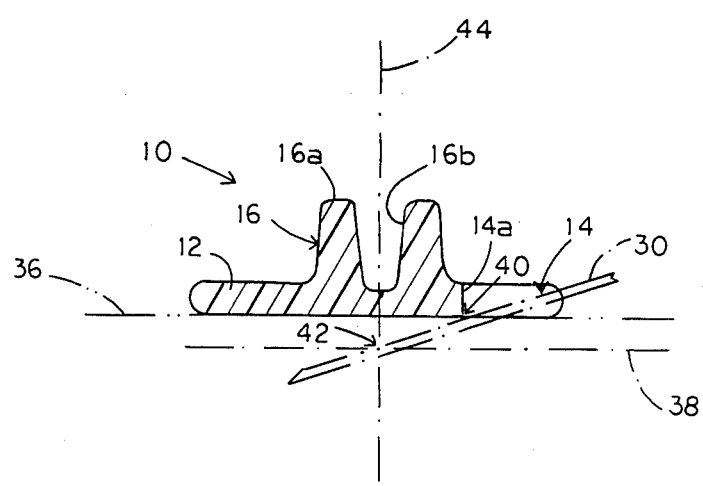
FIG. 2 is a median sectional view through line 2—2 in FIG. 1.

Turning now to the drawings, and particularly FIGS. 1 and 2, a notched pressure pad is shown generally at 10. The pad includes a substantially disc-shaped base 12. A cutout, more specifically a V-shaped notch, shown generally at 14, extends from the periphery or margin of the base towards the center of the base where it terminates at a notch apex 14a. Notch 14, in the preferred embodiment, has a width adjacent the preiphery of the base which is about 1/6 to 1/7 the periphery of the base.

In a typical pad, base 12 has a diameter of from about 1½ to 2 inches. The notch extends a major portion of the distance between the center of the base and the periphery.

A mounting boss 16 is mounted on one side of base 12, and, in the preferred embodiment, is integrally formed with the base. Boss 16 includes a side wall portion 16a which encloses a substantially truncated-conical well 16b. Boss 16 provides means for detachably mounting the pad on an artery clamp.

Figure 3:
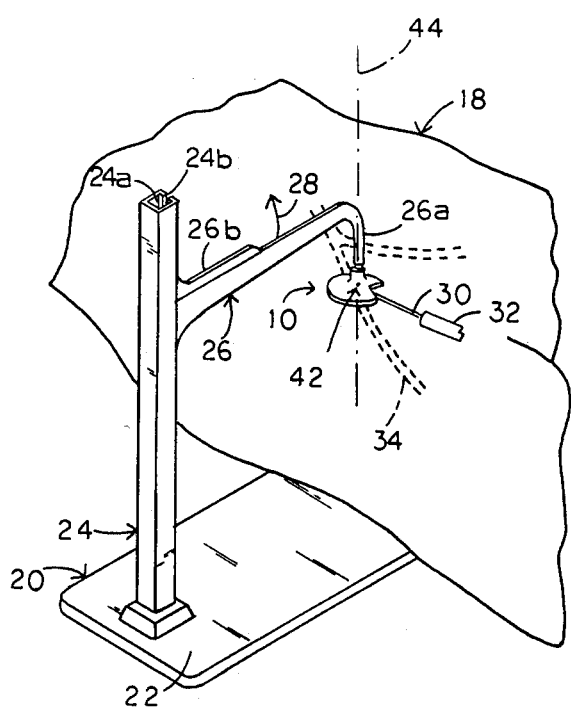
FIG. 3 illustrates the pressure pad of the invention in use with an artery clamp and a catheter in situ.

Turning now to FIG. 3, a notched pressure pad is shown in use on a patient 18 in conjunction with an artery clamp 20.

The artery clamp includes a base portion 22, which supports an elongate upright column 24 which has a hollow core 24a and a slot 24b extending substantially the length of the column. Clamp 20 further includes a pressure pad support arm 26 which is slidably received within column core 24a, and extends through slot 24b. Arm 26 frictionally engages column 24 when upward pressure, as shown by arrow 28, is exerted on a pad-carrying portion 26a of arm 26. An arm release lever 26a facilitates removal and raising of arm 26. Pad 10 is removably mounted on the clamp by inserting portion 26a into truncated-conical well 16b.

Patient 18 in FIG. 3 is depicted undergoing a femoral arterial catheterization procedure. In such a procedure, a catheter, or large needle, is inserted into the patient's femoral artery. In this instance, a catheter 30 which is attached to a catheterization tube 32 is depicted as being inserted into patient 18's right femoral artery 34.

The catheter normally is inserted into the artery of a patient with the catheter extending at a slight incline relative to the skin of the patient. The artery which receives the catheter, while usually close to the skin surface, nevertheless is slightly below the skin surface. As a consequence, the point of entry of the cather into the artery is offset from the point that the catheter enters the skin. This is perhaps best illustrated in FIG. 2 where the skin surface is indicated by the line 36 and the upper surface of the embedded artery is indicated by the line 38. A catheter indicated in outline at 30 enters the skin at point 40 and enters the artery at point 42. Point 42 is offset or displayed from point 40. With the catheter used as illustrated in FIG. 3, this displacement would be toward the head (cranially) of the patient.

Through use of the artery clamp, at some time prior to the end of the arterial catheterization procedure, the clamp is set up as illustrated in FIG. 3. In the femoral catheterization procedure illustrated, the base of the clamp is inserted beneath the patient's buttocks and thigh. Arm 26 of the clamp extends over the patient. Optimally, the pad should be positioned so that the axis 44 of the pad extends through the entry point of the catheter into the artery. The pad should be placed so that it lightly engages the surface of the skin without exerting clamping pressure.

This type of positioning is facilitated with the artery clamp equipped with the pad herein described. Further explaining, the attendant during the procedure is enabled to position the pad with the notch described receiving the catheter where such extends immediately before entering the skin. The notch also provides a visual indicator in that the outline of the notch points to the center of the pad by positioning the pad so that the catheter is in alignment with the general direction of the notch, the axis of the pad also becomes positioned whereby such intersects the catheter at a point offset from where the catheter enters the skin. In practice, this intersection point with the catheter closely approximates where the catheter enters the artery as best illustrated in FIG. 2.

As previously stated, at the completion of the catheterization procedure the catheter is removed. Pressure should then immediately be applied and maintained at the catheter artery entry point for approximately 6-12 minutes, in order to allow for clotting of blood. This application of pressure is most effective if applied directly over the site where the catheter enters the artery.

Using the clamp described, as the catheter is removed, arm 26 is substantially simultaneously moved downward, opposite the direction of arrow 28 in FIG. 3, to a clamping position, where the pad exerts pressure on the artery. The pad in its clamping position is directly over the artery entry point.

If the artery clamp pressure pad were to have a full circular outline, the pressure pad may not be brought down to skin level prior to catheter removal without forcing a portion of the catheter, which is inside the artery, against the anterior artery wall, possibly resulting in damage to the artery.

The capability of nearly simultaneously removing the catheter and applying pressure with an artery clamp assures that the patient will loose a minimum amount of blood. Further, since the pressure pad is placed over the artery entry point prior to catheter removal, the site does not become obscured by blood between the time when the catheter is removed and the pad is positioned over the artery entry point. The quickness of the pressure application also prevents pad slippage due to the presence of blood on the patient's skin.

Thus a new type of artery clamp pressure pad has been disclosed. The pad of the instant invention may be injection molded out of suitable surgically acceptable polymere material, and may further be molded with a sand-blasted or other type of gripping surface on the bottom side of its base, to further prevent slipage of the pad once it is positioned to apply pressure over an arterial entry point.

Although a preferred embodiment of the invention has been described herein, it is understood that variations and modifications may be made without departing from the spirit of the invention.

It is claimed and desired to secure by Letters Patent:

1. A pressure pad for use with an artery clamp at the conclusion of an arterial puncture procedure to facilitate clamping of the arterial puncture site prior to withdrawal from the site of a puncturing implement, said pad comprising a substantially disc-shaped base which includes a notch extending from the periphery of said base towards a central portion of said base, said notch having its largest width at said periphery, and an integral mounting boss attached to said disc for mounting the pad on the artery clamp.

2. The pressure pad of claim 1, wherein said mounting boss is positioned axially centrally of said base, and said notch extends a major portion of the distance beteween said periphery and said boss.

3. The pressure pad of claim 1, wherein the width said notch at said periphery comprises less than 1/6 of the periphery of said base.

4. The pressure pad of claim 1, wherein said notch is substantially V-shaped and is oriented so that the outline thereof points to the center of the disc-shaped base.

* * * * *